March 4, 1941. J. D. BROWNELL Plant Pat. 459
ROSE
Filed July 18, 1940
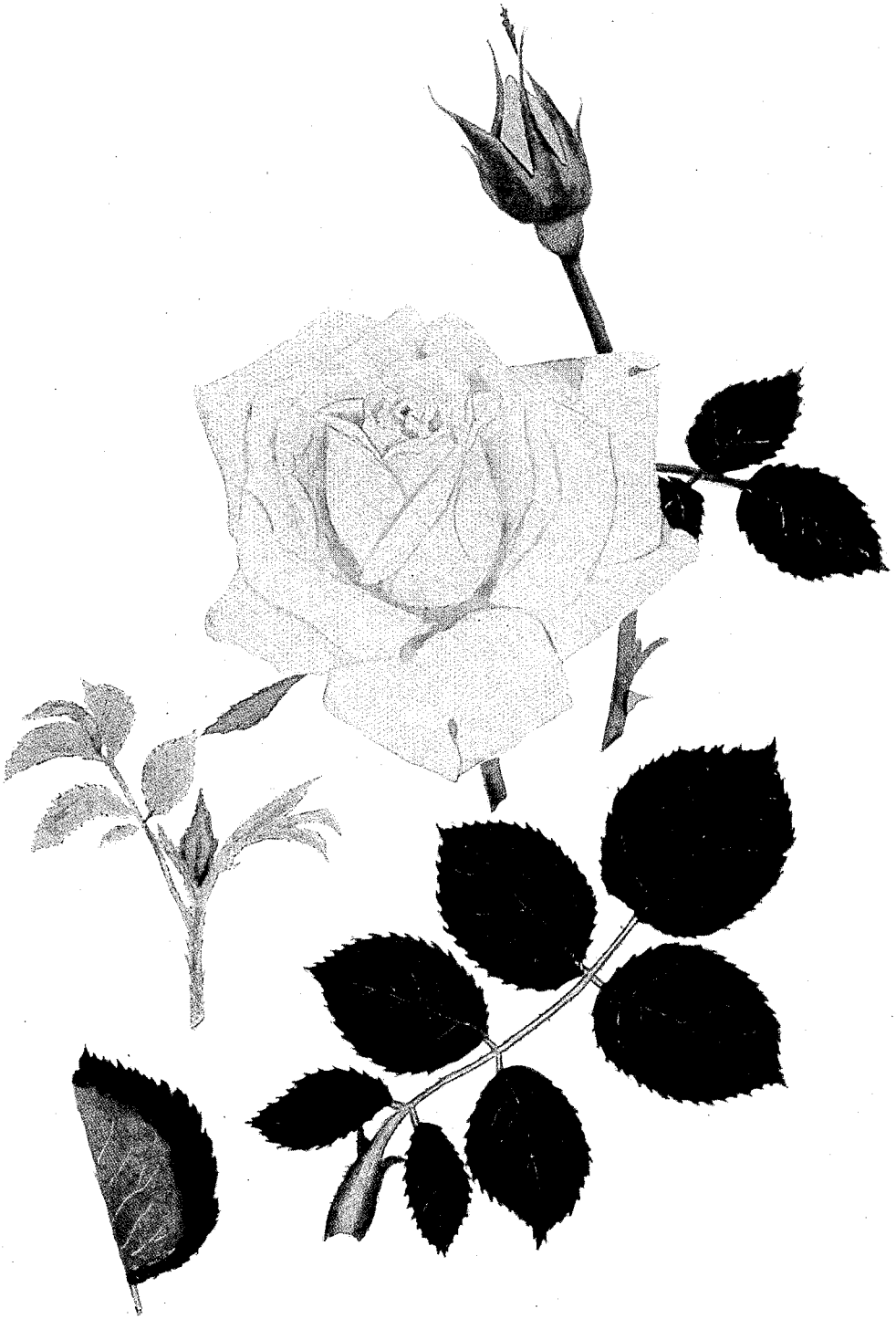
Josephine D. Brownell
INVENTOR.

Patented Mar. 4, 1941

Plant Pat. 459

UNITED STATES PATENT OFFICE

459

ROSE

Josephine D. Brownell, Little Compton, R. I.

Application July 18, 1940, Serial No. 346,163

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by propagation, selection, and cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States;

The red to light pink shades (ordinary dictionary definition) of its petals, in combination with the unique brilliance thereof and their tendency to hold these colors under exposure;

The novelty and variation within certain definite limits of the form of the bloom, its character of holding that form for a long time and the full petallage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom obtains on hybrid teas not having *Rosa wichuraiana* ancestry, but frequently obtains on flower stems of descendants of *Rosa wichuraiana* of the dwarf reblooming type;

And especially its unique characteristic of freedom from defoliation by black-spot, under certain definite conditions of exposure, without any cultural control.

In the accompanying drawing forming a part of this specification I have shown my new rose in its natural colors, that is, as near as is possible to do so artificially.

My new rose is otherwise described as follows:

*Essential information*

Type: Hybrid tea, *Rosa wichuraiana* hybrid, dwarf to ascending to tall to climber, for garden display, cut flower and forcing or growing under glass.

Class: Hybrid tea crossed with *Rosa wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed born on a plant, the parents of which were the variety General McArthur (pollen) and Dr. W. van Fleet (seed). The pollen parent of my new rose was Break O'Day.

The pollenation that fertilized the seed that grew into my new rose, as well as the pollenation that produce its two parents were directed and were performed by emasculating flowers and placing thereon a bag protecting from self and foreign pollen. These bags were later removed and the flowers were hand pollenated with a camel's hair brush and the bags immediately replaced. The date of this pollenation was June 29, 1935.* The seed was planted under my direction on December 18, 1935, and the date of the first flower was July 15, 1936.

The plant and flower seemed to me to be of unusual merit and I have since made and directed extensive propagations and tests thereof in the United States and in foreign countries.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1936–39 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one and frequently two or three and occasionally more on each stem, in the usual hybrid tea type of cluster. The pedicels and peduncles are medium in diameter and length, erect, stiff, almost smooth, free from large prickles and bristles but with a few very small prickles varying to small hairs. Stems are long, diameter medium to slightly large and notably stiff and rigid.

*This and other dates herein are approximate.

Quantity of bloom: Free to abundant, being cumulative in quantity from year to year as the plant increases in size, notably free flowering through the summer, being of greater bloom quantity than that of tender hybrid teas known to me.

Fragrance: Strong, distinctive, pleasing china tea in combination with that of *Rosa wichuraiana* and musk, under favorable environment.

Bud: Neck normal as described, opens well, being little to not at all affected by hot or wet weather or both, as to color is less intense and the form of the petals is less recurled.

Before the calyx breaks the size is medium, form moderately pointed, frequently with one or more sepals having foliaceous parts extending beyond the apex of the calyx up to about three quarters of an inch, the number and size of the foliaceous parts being variable and frequently having one narrow, pointed, serrate appendage on each side of the sepals, otherwise the sepals are usually normal and regular, tapering to lanceolate at their apex, turning back nearly perpendicular to the pedicel as the bud opens.

Color of the bud as the calyx opens; both sides of petals variable between Blood Red at (3) (reference to color chart, The Rose Manual 1930 by J. H. Nicolas, opposite page 264) and Garnet at (2) (same reference).

Bloom: As the bud opens and the flower develops to maturity the color both sides of the petals gradually changes to Lilac Pink at (3) Plate III opposite page 262 (same reference as last), except that the outer sides of the petals retain somewhat longer than do the inner sides some of the Blood red coloring. The base of the petals in their later stage is variously overlaid with Carmine (same as last reference). The petals have a characteristic brilliance.

The flower is usually 4 to 5 inches in diameter when fully open, infrequently more or less, very double having petals variable in number, usually from 40 to 60 with some narrow petals and petaloids in the center, variable in number.

The flower opens high centered, recurled, not showing the stamens and pistils until late maturity. The petals are variable from obovate to ovate with inner petals narrower to irregular variable forms. Outer and intermediate petals except in extreme hot temperatures recurl outward, frequently notably notched once at the apex. Texture is medium to thick and leathery; both sides satiny; with slight veining which is scarcely noticeable. The time of opening in favorable conditions is three to five days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Productive organs: Stamens, quantity variable, usually few to medium, quantity indirectly proportional to the number of petals, of slightly uneven length.

Anthers, Light Salmon Orange (this and references hereinafter to color are to Ridgway).

Filaments, nearly Mustard Yellow.

Pistils are several of slightly uneven length, somewhat more than ½ inch long.

Ovaries are usually all inclosed, infrequently one protrudes.

Hips frequently develop ovoid to globular, color comparable with under side of leaves with variable colored overlay on the side exposed to the sun, moderately smooth; walls thin, fleshy.

Sepals are persistent and break off easily.

Seeds variable in number; germination to date about 10% over a variable period.

*Plant*

Foliage: Is abundant, of compound leaves of three to five leaflets near the flower, five leaflets lower down the stem and frequently seven leaflets nearer the base. Size of leaflets medium to small, averaging in size a little larger than half way between the average hybrid tea and the *Rosa wichuraiana* leaflets. Form of leaflets usually ovate with apex moderately acute, base rounded frequently slightly acute, in some instances with the circumference on one side of the petiolules out of alignment with the other side by about one-sixteenth of an inch, margins with fine pointed serrations, petiolules short.

Color of leaflets on the upper surface is slightly variable from Dark Dull Yellow Green, with reverse side nearly Asphodel Green overlaid with Dahlia Carmine. The young growth more nearly compares on both sides with the color of the under sides of the leaflets, with edges and mid-ribs nearly Indian Red.

The rachises are medium, moderately narrow to slender, upper side smooth except some very short hairs on edges. Under side moderately smooth, usually 3 to 5 short prickles.

Stipules are medium in length averaging slightly under three-quarters of an inch long, with small short points, the upper edges of which when spread in the same plane make an angle of about 100 degrees.

*Disease.*—This rose variety is more free from defoliation on account of black-spot and mildew than is any other hybrid tea variety known to me, and from many testing areas under varied exposures, no such defoliation has been noted during the growing season.

Growth: Habit, dwarf, compact, becoming bushy to tall; more cumulative in growth from year to year than the normal hybrid tea rose plant, by stems or canes from the base and by rebranching and growth and enlargement and extension of the stems. The growth is moderately free at first, developing more rapidly after one or two years under favorable vegetative opportunity.

Color of mature stems is the same as that of the upper surface of mature leaves, shading variously lighter and also with overlay of Indian Red variable in intensity.

Prickles, several, usually three between leaves averaging in length about three-eighths of an inch, shading from Dahlia Carmine to lighter at the base, turning lighter throughout and later to nearly colorless. Hairs on upper portions of stems usually same color as prickles. Tip of very young branches color of prickles rapidly changing to color of main stems.

Winter resistance: A notable characteristic of this new rose is its resistance to moderate sub-zero temperatures in combination with its hybrid tea characters and its *Rosa wichuraiana* ancestry. This variety with grafted bud and plant above entirely exposed above ground to moderate sub-zero temperatures survived and bloomed normally the following season. The word "temperature" herein refers to the Fahrenheit scale.

Longevity: As a natural consequence of the foregoing described characters the expected longevity of the plants of this new variety is substantially greater than that of normal hybrid teas and from tests and data obtained from this variety and from others of comparable parentage, it has the probable expectancy of several times that of the average hybrid tea plant in commerce.

Comparisons: Probably the best known roses in commerce comparable with this new variety are Radiance and Red Radiance. My new variety as compared with them is in color about a combination of the two, with a slight addition of Carmine and Blood Red variable throughout. Of petals it usually has about ten more. In form, it is more recurled. The flower averages slightly larger and has a more spicy fragrance, it keeps longer and holds a deeper color longer, it can be grown to bloom and rebloom more than 50% more. The plant is more cumulative in growth from year to year, can be grown into a larger plant. The foliage is smaller and more abundant, frequently with two more leaflets forming the leaves. Under exposure to black-spot this new variety is free from defoliation without control while the other two are not. It will survive after exposure to colder temperatures, to flower normally thereafter.

I claim:

The rose variety substantially as shown and described, characterized by its new and distinctive constitution, including resistance to winter injury, its intensity and continuity of florescence, its pleasing fragrance, its long keeping character of the color of its petals and the form of its petals and the form of the flower, variable within certain definite limits, its character of long holding that form, its color varying from nearly Garnet to Lilac Pink, all in association with its habit of branching from bloom stems and from the base and blooming in the hybrid tea manner and its freedom from defoliation by black-spot during the growing season.

JOSEPHINE D. BROWNELL.